(12) United States Patent
Burie et al.

(10) Patent No.: US 7,254,291 B2
(45) Date of Patent: Aug. 7, 2007

(54) OPTICAL INTERFEROMETER

(75) Inventors: Jean-Rene Burie, Bruyeres le Chatel (FR); Ali Guermache, Nozay (FR)

(73) Assignee: Avanex Corporation, Fremont, CA (US)

( * ) Notice: Subject to any disclaimer, the term of this patent is extended or adjusted under 35 U.S.C. 154(b) by 0 days.

(21) Appl. No.: 11/217,543

(22) Filed: Sep. 1, 2005

(65) Prior Publication Data

US 2006/0215953 A1 Sep. 28, 2006

(51) Int. Cl.
*G02B 6/122* (2006.01)
*G01B 9/02* (2006.01)

(52) U.S. Cl. .............................. 385/14; 385/28; 385/39; 356/480; 359/337.5

(58) Field of Classification Search ...................... None
See application file for complete search history.

(56) References Cited

U.S. PATENT DOCUMENTS 6,771,847 B2 * 8/2004 Mukai .......................... 385/14

OTHER PUBLICATIONS

Xioa Y, et al. "An MMI-Based Demultiplexer with Reduced Crosstalk" Optics Communications, North-Holland Publishing Co. Amsterdam, NL, vol. 247, No. 4-6, Mar. 15, 2005, pp. 335-339, XP004793147, ISSN: 0030-4018.

Soldano L. B. et al. "Optical Multi-Mode Interference Devices Based on Self-Imaging: Principles and Applications" Journal of Lightwave Technology, IEEE, Service Center, New York, NY, US, vol. 13, No. 4, Apr. 1, 1995, pp. 615-627, XP000513578 ISSN: 0733-8724.
Paiam, M. R. et al. "Compact Planar 980/1550-NM Wavelength Multi/Demultiplexer Based on Multimode Interference" IEEE Photonics Technology Letters, IEEE Service Center, Piscataway, NJ, US, vol. 7, No. 10, Oct. 1, 1995, pp. 1180-1182, XP000537230, ISSN: 1041-1135.
EP Search Report, Application No. 05108569.4, Dated Jun. 8, 2006.

* cited by examiner

*Primary Examiner*—Michelle Connelly-Cushwa
*Assistant Examiner*—Jerry T. Rahill
(74) *Attorney, Agent, or Firm*—Patterson & Sheridan, LLP (57) ABSTRACT

One embodiment of an optical interferometer includes a first MMI device coupled to a second MMI device via a waveguide. The first MMI device separates a first signal into a guided portion and a diffused portion. The guided portion is transmitted to the second MMI device through the waveguide. At least part of the diffused portion reflects off a reflector towards the second MMI device and is coupled with the guided portion within either the second MMI device or a part of the waveguide proximal to the second MMI device, forming at least part of a second signal. The difference between the propagation times of the guided portion and the at least part of the diffused portion results in constructive or destructive interference between the two portions, allowing specific channels to be added to or dropped from the first signal.

21 Claims, 9 Drawing Sheets

OPTICAL INTERFEROMETER

CROSS-REFERENCE TO RELATED APPLICATIONS

This application claims benefit of European patent application serial number EP 05300219.2, filed Mar. 23, 2005, which is herein incorporated by reference.

BACKGROUND OF THE INVENTION

1. Field of the Invention

The present invention relates generally to the field of fiber optics and more specifically to a new optical interferometer design.

2. Description of the Related Art

Optical interferometers are well-known devices in which two or more light waves are coupled together to produce either destructive or constructive interference. These optical devices are typically used for a wide variety of functions within optical systems and subsystems. For example, some types of optical interferometers, such as Fabry-Perot interferometers, are used as filter devices, while other types of optical interferometers are used for optical switching. In addition, multimode interferometers (MMIs) may be implemented as splitters, couplers, filters or multiplexers.

Many types of interferometers are realized on silicon or other like substrates. Forming optical interferometers on a substrate allows more than one interferometer to be implemented on a single die, thereby increasing overall design density. One drawback of adding multiple interferometers on a single die, however, is that light diffused from one interferometer may be unintentionally coupled with the light of another interferometer, thereby causing unwanted interference between the light. To prevent such unwanted coupling, interferometers must be adequately spaced apart on the die or blockers must be used to block the light diffused from each interferometer. Such solutions are problematic because they either increase the overall size of the design or add complexity and cost to the design.

As the foregoing illustrates, what is needed in the art is an interferometer design that overcomes the drawbacks of current interferometer designs described above.

SUMMARY OF THE INVENTION

One embodiment of an optical interferometer includes a first MMI device optically coupled to a second MMI device via a waveguide. The first MMI device is configured to separate a first signal into a guided portion and a diffused portion. The guided portion is transmitted to the second MMI device through the waveguide. At least part of the diffused portion reflects off the reflector towards the second MMI device and is coupled with the guided portion within either the second MMI device or a part of the waveguide disposed proximally to the second MMI device to form at least part of a second signal. The difference between the propagation times of the guided portion and the at least part of the diffused portion results in constructive or destructive interference between the two portions.

One advantage of the disclosed interferometer is that it may be configured to add or drop specific channels to or from the first signal. The interferometer may also be configured as a gas sensor or material detector.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
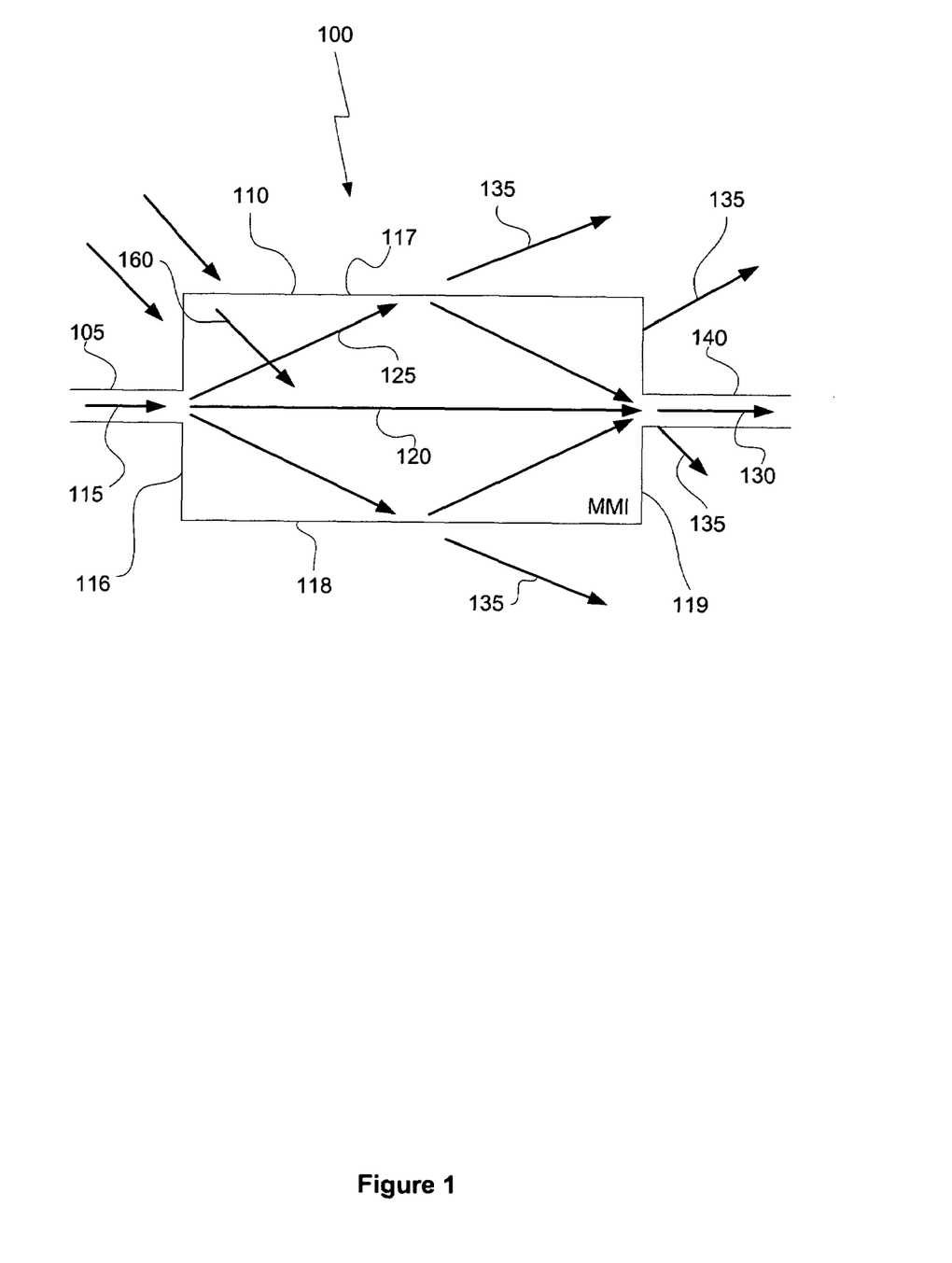
FIG. 1 is a conceptual diagram of an MMI device, according to one embodiment of the invention.

FIG. 1 is a conceptual diagram of an MMI device 100, according to one embodiment of the invention. As shown, the MMI device 100 includes, without limitation, a first waveguide 105, a second waveguide 140 and a multimode section 110. In one embodiment, each of the first waveguide 105 and the second waveguide 140 may comprise a monomode optical fiber. The first waveguide 105 is coupled to the multimode section 10 and is configured as the input port of the multimode section 110. The second waveguide 140 also is coupled to the multimode section 110 and is configured as the output port of the multimode section 110. The multimode section 110 includes walls 117 and 118 and faces 116 and 119.

In operation, a signal 115 is transmitted to the multimode section 110 through the first waveguide 105. Upon entering the multimode section 110, the signal 115 diffracts, separating into a first portion 120 and a second portion 125. The first portion 120 is transmitted directly to the second waveguide 140. The second portion 125, however, is reflected by the walls 117 and 118 and is then coupled with the first portion 120 at or near the second waveguide 140 (i.e., the output port). Since the second portion 125 follows a different optical path between the input port and the output port than the first portion 120, the propagation time of the second portion 125 between the input port and the output port is different than the propagation time of the first portion 120. Consequently, constructive or destructive interference may result from the phase difference between the first portion 120 and the second portion 125 as the second portion 125 is coupled with the first portion 120 at or near the output port. The recombined signal forms the guided portion 130 (of the original signal 115), which is transmitted out of the multimode section 110 through the second waveguide 140.

The second portion 125 oftentimes is not completely reflected by walls 117 and 118. Rather, part of the second portion 125 may diffuse across the walls 117 and 118, forming a diffused portion 135 of the original signal 115. The diffused portion 135 may also diffuse across the face 119 or the second waveguide 140, as illustrated in FIG. 1, depending on the specific design of the multimode section 110. The MMI device 100 also may be configured such that incoming optical signals 160 are coupled with the signal 115 within the multimode section 110. In various embodiments, the optical signals 160 may enter the multimode section 110 through the face 116, the walls 117 and/or 118, the first waveguide 105 or any combination thereof.

Thus, as is well-known, the MMI device 100 may be configured (i) to separate a signal or combination of signals input into the multimode section 110 into a guided portion 120 and a diffused portion 135 and/or (ii) to couple different optical signals input into the multimode section 110. Further, as persons skilled in the art also understand, the MMI device 100 may be configured to precisely control the amount of transmitted light (represented by the guided portion 130), diffused light (represented by the diffused portion 135) and reflected light (not shown) generated from a given input signal 115 or from a given combination of input signal 115 and optical signals 160.

Figure 2:
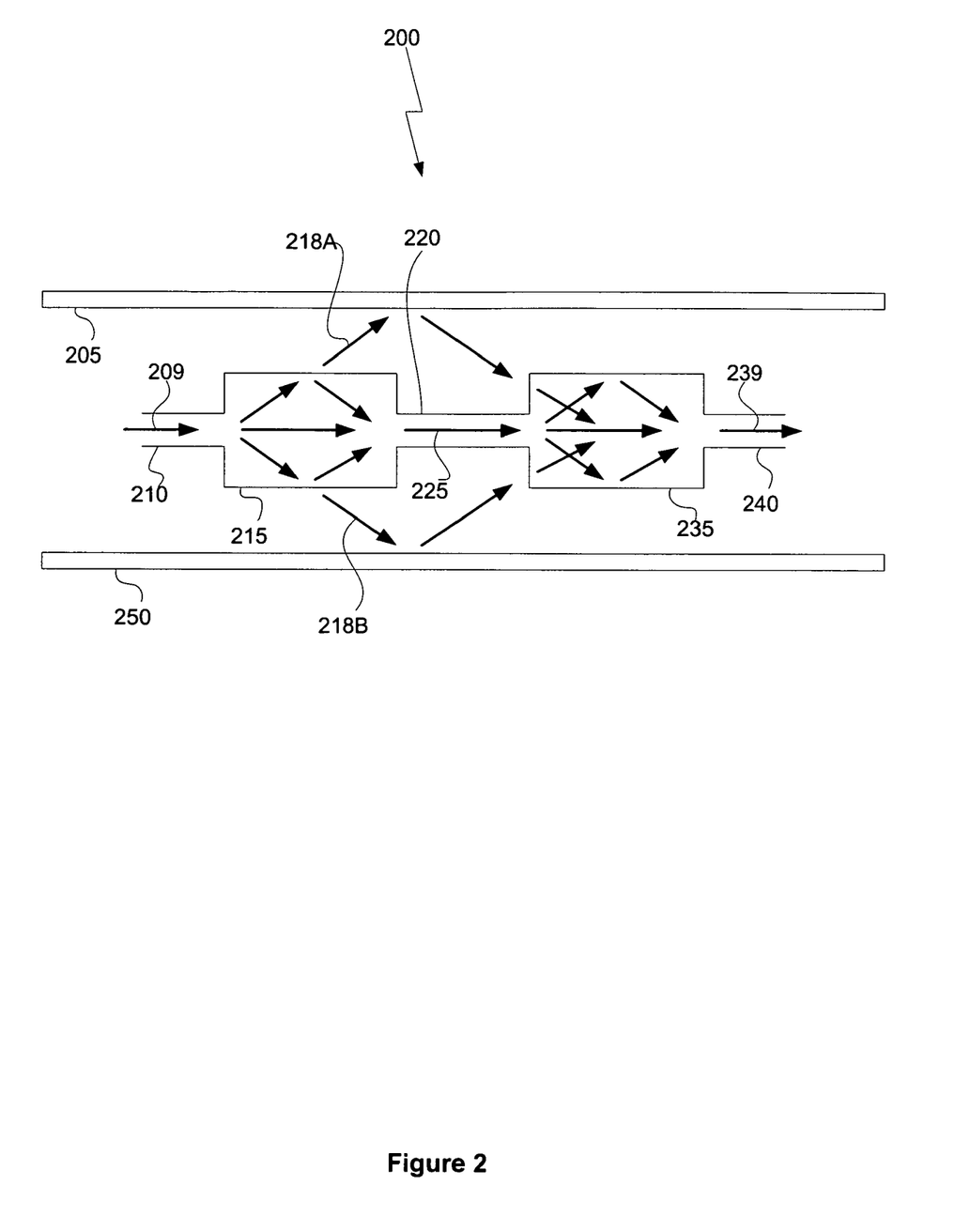
FIG. 2 is a conceptual diagram of an optical interferometer, according to one embodiment of the invention.

FIG. 2 is a conceptual diagram of an interferometer 200, according to one embodiment of the invention. The interferometer 200 includes, without limitation, a first MMI device 215, a second MMI device 235, a first waveguide 210, a second waveguide 220, a third waveguide 240, a first reflector 205 and a second reflector 250. The first waveguide 210 is coupled to the first MMI device 215 and is configured as an input port of the interferometer 200. The first MMI device 215 is coupled to the second MMI device 235 via the second waveguide 220. The third waveguide 240 is coupled to the second MMI device 235 and is configured as an output port of the interferometer 200.

In operation, a first signal 209 is input into the first MMI device 215 via the first waveguide 210. The first MMI device 215 is configured to separate the first signal 209 into a guided portion 225 and diffused portions 218A and 218B. The guided portion 225 is transmitted from the first MMI device 215 to the second MMI device 235 via the second waveguide 220. The diffused portions 218A and 218B diffuse from the first MMI device 215, as shown, and are reflected towards the second MMI device 235 by the first reflector 205 and the second reflector 250, respectively. The second MMI device 235 is configured to couple the guided portion 225 with the diffused portions 218A and 218B to form a second signal 239, which is output from the second MMI device 235 via the third waveguide 240.

Since the optical path of the diffused portions 218A and 218B is different from the optical path of the guided portion 225, the propagation times of the diffused portions 218A and 218B and the guided portion 225 are different. The phase difference caused by the difference in the propagation times may result in either constructive or destructive interference between the diffused portions 218A and 218B and the guided portion 225 within the second MMI device 235. This interference can be precisely controlled to achieve either constructive or destructive interference within a specific wavelength or channel by adjusting one or more design parameters associated with the interferometer 200. These design parameters are described in greater detail below in conjunction with FIG. 3.

As described, in one embodiment, optical interferometer 200 is configured such that diffused portions 218A and 218B are coupled with guided portion 225 within the second MMI device 235. However, in alternative embodiments, optical interferometer 200 may be configured such that diffused portions 218A and 218B are coupled with guided portion 225 within a part of second waveguide 220 disposed in close proximity to second MMI device 235 or within both a part of second waveguide 220 and the second MMI device 235. In addition, the interferometer 200 may alternatively include only one reflector. Further, the reflector may have a cylindrical or other shape that enables the arrangement of the MMI devices and the reflective surfaces to be non-planar.

Figure 3:
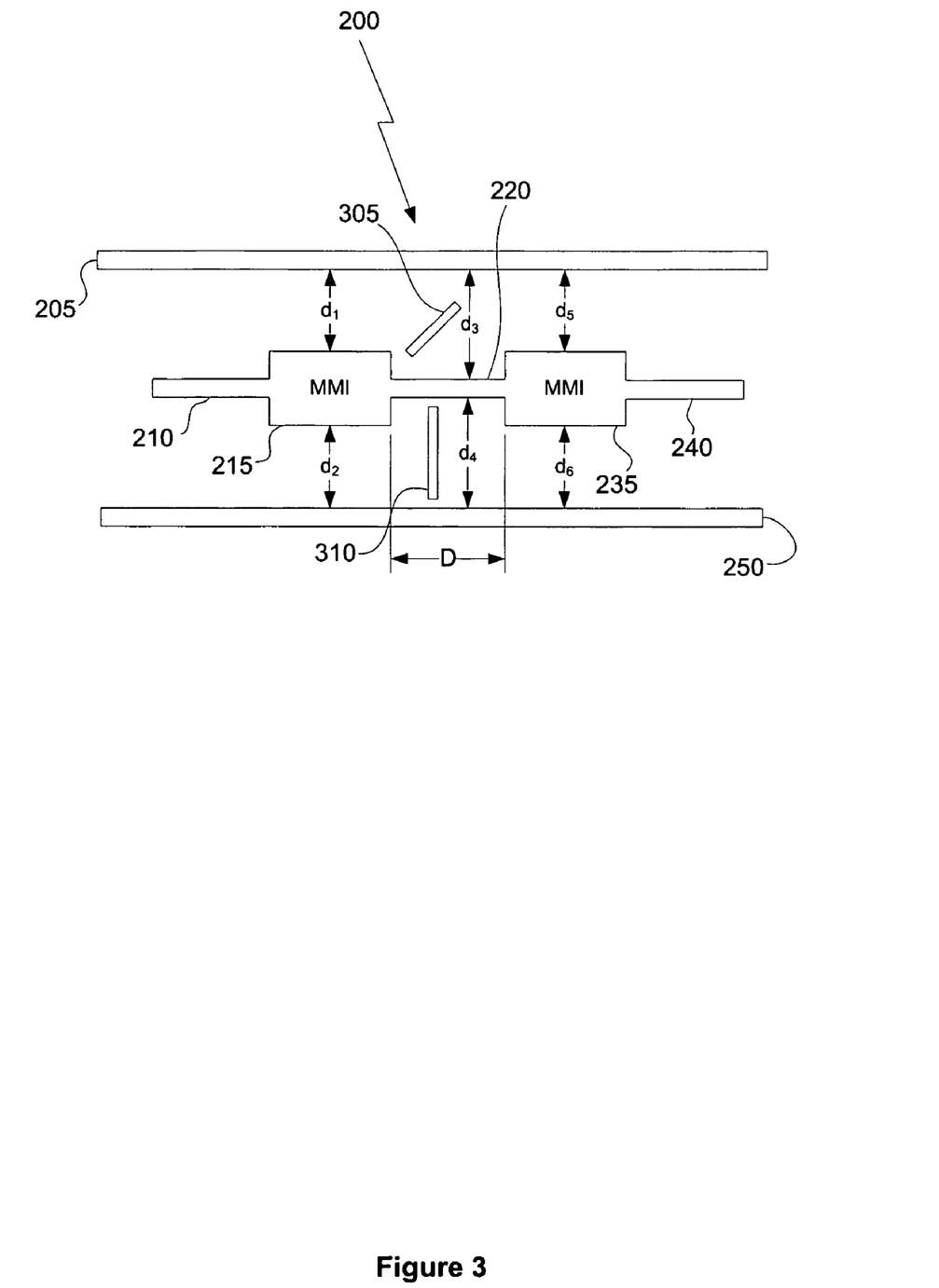
FIG. 3 illustrates certain design parameters associated with the interferometer of FIG. 2, according to one embodiment of the invention.

FIG. 3 illustrates certain design parameters associated with the interferometer 200 of FIG. 2, according to one embodiment of the invention. As shown, the distance from the first MMI device 215 to the first reflector 205 is $d_1$, and the distance from the first MMI device 215 to the second reflector 250 is $d_2$. Similarly, the distance from the second MMI device 235 to the first reflector 205 is $d_5$, and the distance from the second MMI device 235 to the second reflector 250 is $d_6$. The distance from the second waveguide 220 to the first reflector 205 is $d_3$ and the distance from the second waveguide 220 to the second reflector 250 is $d_4$. Finally, the distance from the first MMI device 215 to the second MMI device 235 is D.

Figure 4:
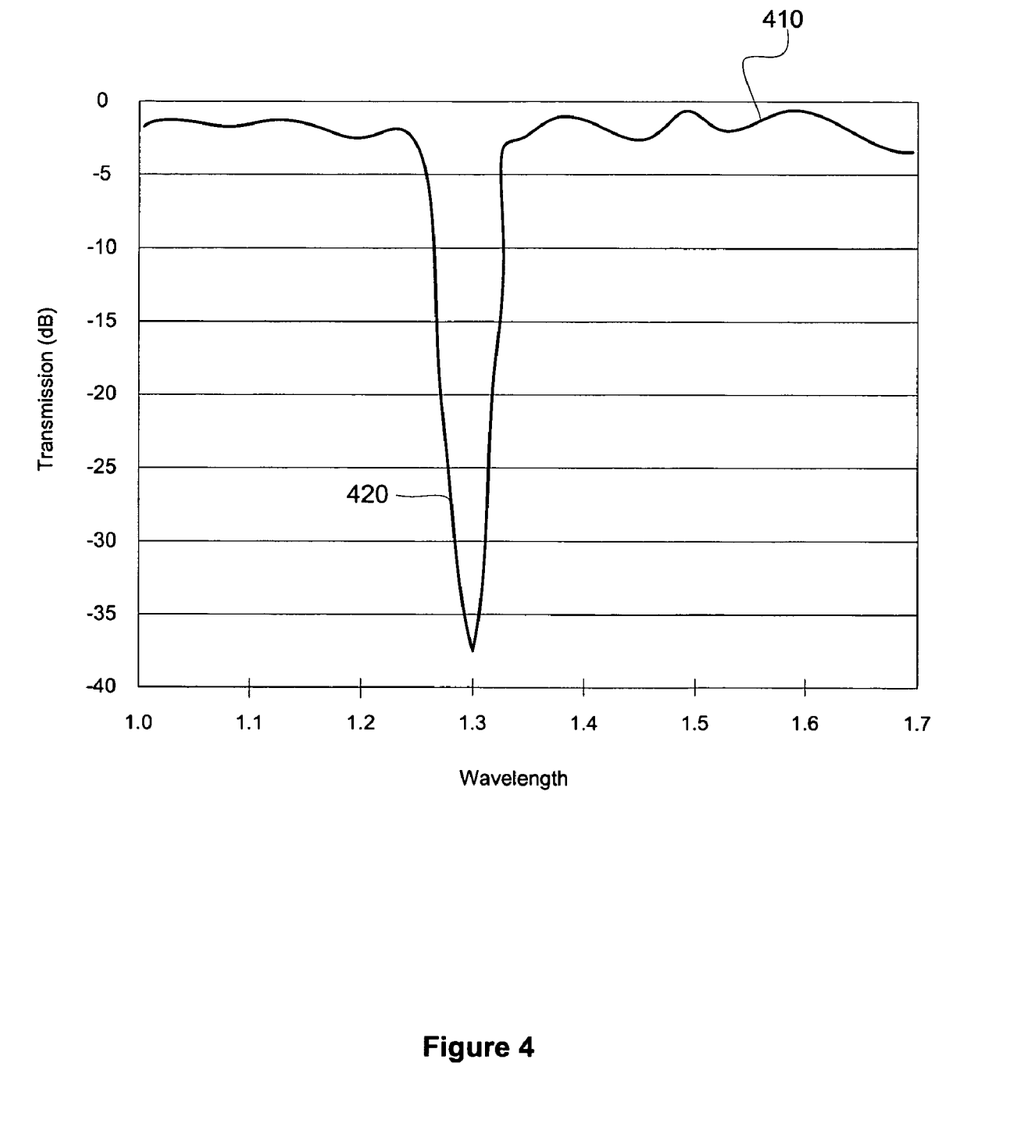
FIG. 4 is a graphical diagram illustrating a transmission response curve of the optical interferometer of FIG. 2 when configured as a drop filter.
Figure 5:
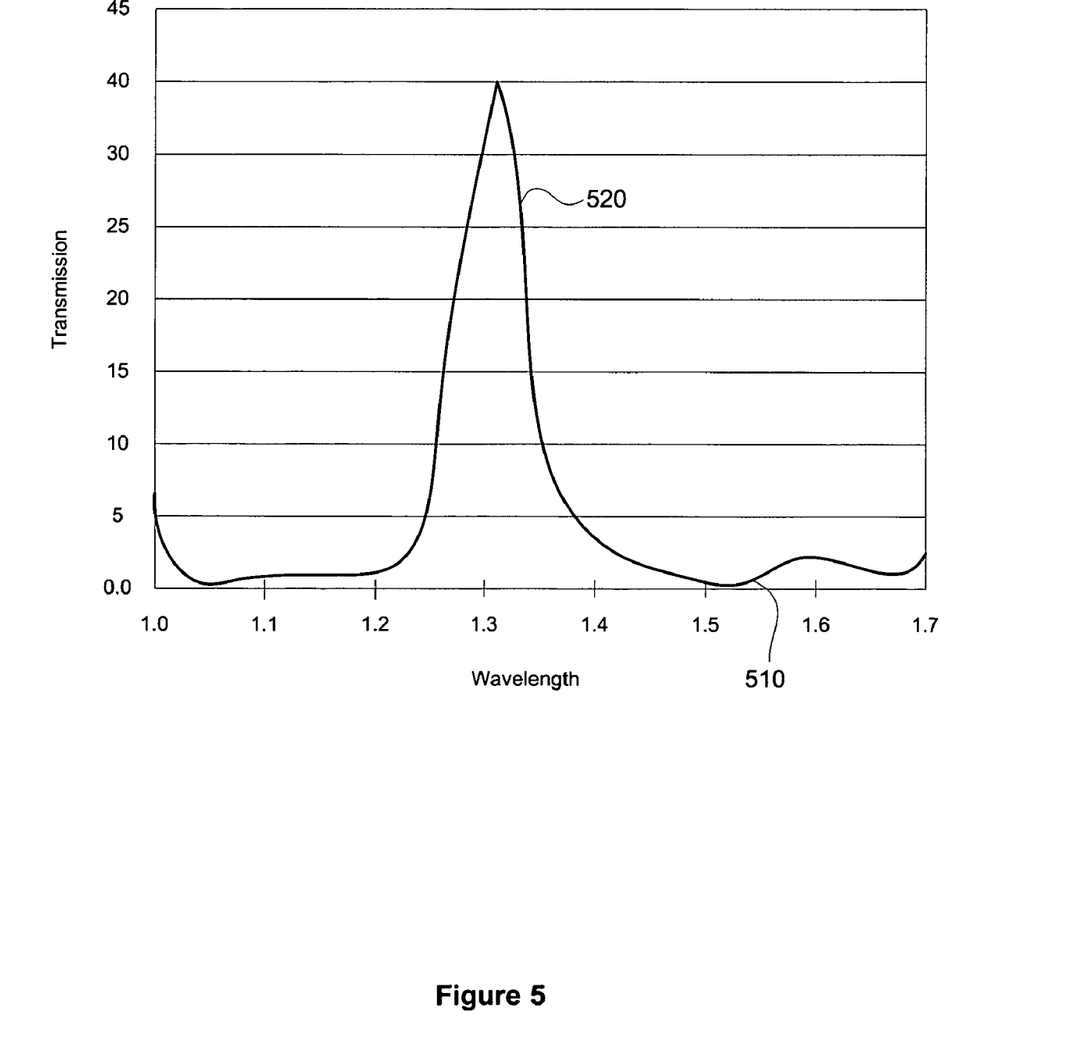
FIG. 5 is a graphical diagram illustrating a transmission response curve of the optical interferometer of FIG. 2 when configured as a bandpass filter.

The parameters $d_1$, $d_2$, $d_3$, $d_4$, $d_5$, $d_6$ and D affect the length of the optical path followed by the diffused portions 218A and 218B between the first MMI device 215 and the second MMI device 235. Likewise, the parameter D affects the length of the optical path followed by the guided portion 225 between the first MMI device 215 and the second MMI device 235. Since the propagation times of the diffused portions 218A and 218B and the guided portion 225 between the first MMI device 215 and the second MMI device 235 are directly related to the lengths of their respective optical paths, the propagation times of the diffused portions 218A and 218B and the guided portions 225 may be controlled by controlling the lengths of their respective optical paths. Similarly, the phase difference between the diffused portions 218A and 218B and the guided portion 225 resulting from their different propagation times may be controlled by controlling the lengths of their respective optical paths. As persons skilled in the art will recognize, the phase difference between the diffused portions 218A and 218B and the guided portion 225 affects the amount and type of interference between the diffused portions 218A and 218B and the guided portion 225 when coupled together within the second MMI device 235. Thus, by precisely controlling the lengths of the respective optical paths, one can precisely control whether the diffused portions 218A and 218B and the guided portion 225 constructively or destructively interfere with one another and which wavelengths or channels are affected by that interference. FIGS. 4 and 5, below, provide examples of the various types of interference that may be achieved using the interferometer 200.

As is well-known, if the distance, D, is large (e.g. greater than 200 um), then the coupling between the diffused portions 218A and 218B and the guided portion 225 within the second MMI device 235 may be substantially reduced since the intensity of the diffused light may be attenuated by the relatively longer optical path between the first MMI device 215 and the second MMI device 235. Another way to reduce or eliminate the coupling between diffused portion 218A and 218B and guided portion 225 is to use either a reflecting device 305 or an absorbing device 310, as shown in FIG. 3, to reflect the diffused portions 218A and 218B away from the second MMI device 235 or to absorb all or part of the diffused portions 218A and 218B. The amount of diffused light also may be reduced or eliminated by adding reflective coating to the first MMI device 215 and/or second waveguide 220. Controlling the quantity and intensity of the diffused light gives the designer yet another means to control the interference between the diffused portions 218A and 218B and the guided portion 225 and, thus, the transmission response of the interferometer 200.

In an alternative embodiment, a tunable interferometer may be constructed by using micro-electrical-mechanical systems (MEMS) to control the parameters $d_1$, $d_2$, $d_3$, $d_4$, $d_5$, $d_6$ and D. For example, the first reflector 205 and the second reflector 250 may be positioned by MEMS to control $d_1$, $d_2$, $d_3$, $d_4$, $d_5$, and $d_6$. Similarly, a MEMS may be used to control the distance, D, between the first MMI device 215 and the second MMI device 235. The MEMS then may be used to modify the lengths of the optical paths followed by the diffused portions 218A and 218B and the guided portion 225, thereby modifying the interference between these portions within the second MMI device 235 and, thus, the transmission response of the interferometer 200.

FIG. 4 is a graphical diagram illustrating a transmission response curve 410 of the optical interferometer 200 of FIG. 2 when configured as a drop filter. In this embodiment, the interferometer 200 is configured to attenuate or "drop" a channel corresponding to a wavelength of 1.3 nm from the optical signal 209 input into the interferometer 200. As shown, the dropped channel is represented by an inverted spike 420 in the transmission response curve 410. As described above in FIG. 3, by selecting the design parameters of the interferometer 200 appropriately, the destructive interference between the diffused portions 218A and 218B and the guided portion 225 necessary to attenuate or drop the pre-selected channel may be achieved. Again, in other embodiments, the interferometer 200 may be configured to drop any channel or range of wavelengths from the optical signal 209 by selecting design parameters such that the destructive inference necessary to drop the desired channel or range of wavelengths is achieved.

Although not shown, in other alternative embodiments, the interferometer 200 also may be configured to "add" a channel or range of wavelengths to the optical signal 209 by selecting design parameters such that the constructive interference between the diffused portions 218A and 218B and the guided portion 225 necessary to augment the desired channel or range of wavelengths is achieved. The transmission response curve 410 would show a spike (instead of the inverted spike 420) for each added or augmented channel.

FIG. 5 is a graphical diagram illustrating a transmission response curve 510 of the optical interferometer 200 of FIG. 2 when configured as a bandpass filter. In this embodiment, the interferometer 200 is configured to "pass" a channel corresponding to a wavelength of 1.3 nm from the optical signal 209 input into the interferometer 200, while attenuating the other channels. As shown, the passed channel is represented by a spike 520 in the transmission response curve 510. Again, by selecting the appropriate design parameters, the destructive interference between the diffused portions 218A and 218B and the guided portion 225 necessary to pass the pre-selected channel may be achieved. In other embodiments, the interferometer 200 may be configured to pass any channel or channels of the input signal 209 by selecting design parameters such that the destructive interference necessary to pass the desired channel or channels is achieved.

In yet other alternative embodiments, the interferometer described herein may be designed to include more than two MMI devices. As described in greater detail below in FIGS. 6 and 7, such a configuration provides the interferometer with, among other things, the ability to add or drop multiple channels to or from an optical signal input into the interferometer.

Figure 6:
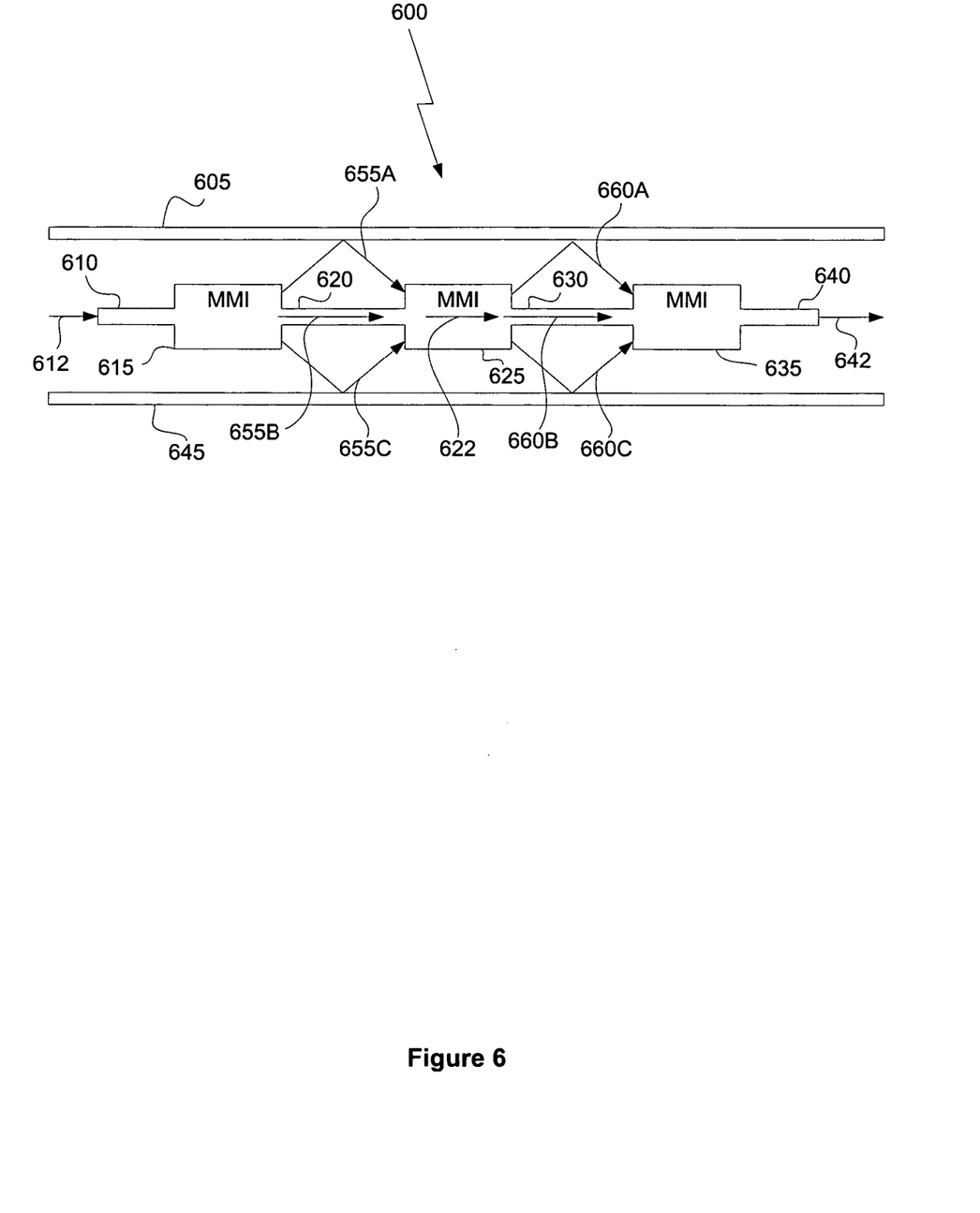
FIG. 6 is a conceptual diagram of an optical interferometer, according to a second embodiment of the invention.

FIG. 6 is a conceptual diagram of an optical interferometer 600, according to a second embodiment of the invention. As shown, the interferometer 600 includes, without limitation, a first MMI device 615, a second MMI device 625, a third MMI device 635, a first waveguide 610, a second waveguide 620, a third waveguide 630, a fourth waveguide 640, a first reflector 605 and a second reflector 645. The first waveguide 610 is coupled to the first MMI device 615 and is configured as an input port of the interferometer 600. The first MMI device 615 is coupled to the second MMI device 625 via the second waveguide 620. The second MMI device 625 is coupled to the third MMI device 635 via the third waveguide 630. The fourth waveguide 640 is coupled to the third MMI device 635 and is configured as an output port of the interferometer 600.

In operation, a first signal 612 is input into the interferometer 600 via the first waveguide 610. The first MMI device 615 is configured to separate the first signal 612 into a guided portion 655B and diffused portions 655A and 655C. The guided portion 655B is transmitted from the first MMI device 615 to the second MMI 625 device via the second waveguide 620. The diffused portions 655A and 655C diffuse from the first MMI device 615, as shown, and are reflected towards the second MMI device 625 by the first reflector 605 and the second reflector 645, respectively. The second MMI device 625 is configured both to couple and to separate optical signals. Thus, the second MMI device 625 is configured to couple the guided portion 655B with the diffused portions 655A and 655C to form a second signal 622. The second MMI device 625 also is configured to separate the second signal 622 into a guided portion 660B and diffused portions 660A and 660C. The guided portion 660B is transmitted from the second MMI device 625 to the third MMI device 635 via the third waveguide 630. The diffused portions 660A and 660C diffuse from the second MMI device 625, as shown, and are reflected towards the third MMI device 635 by the first reflector 605 and the second reflector 645, respectively. The third MMI device 635 is configured to couple the guided portion 660B with the diffused portions 660A and 660C to form a third signal 642, which is output from the third MMI device 635 via the fourth waveguide 640.

As described above in FIG. 3, by controlling the distances between the first and second reflectors 605 and 645 and the first MMI device 615 and the second MMI device 625 as well as the distance between the first MMI device 615 and the second MMI device 625, one may control the propagation times of the diffused portions 655A and 655C and the guided portion 655B between the first MMI device 615 and the second MMI device 625. Likewise, by controlling the distances between the first and second reflectors 605 and 645 and the second MMI device 625 and the third MMI device 635 as well as the distance between the second MMI device 625 and the third MMI device 635, one may control the propagation times of the diffused portions 660A and 660C and the guided portion 660B between the second MMI device 625 and the third MMI device 635. As previously explained herein, by controlling the propagation times, one may precisely control (i) whether the diffused portions 655A and 655C and the guided portion 655B constructively or destructively interfere with one another within the second MMI device 625 as well as which wavelengths or channels are affected by the interference and (ii) whether the diffused portions 660A and 660C and the guided portion 660B constructively or destructively interfere with one another within the third MMI device 635 as well as which wavelengths or channels are affected by the interference. The ability to control optical interference on more than one level enables the interferometer 600 to be configured to provide more complex transmission responses—transmission responses that may affect, for example, multiple channels.

Figure 7:
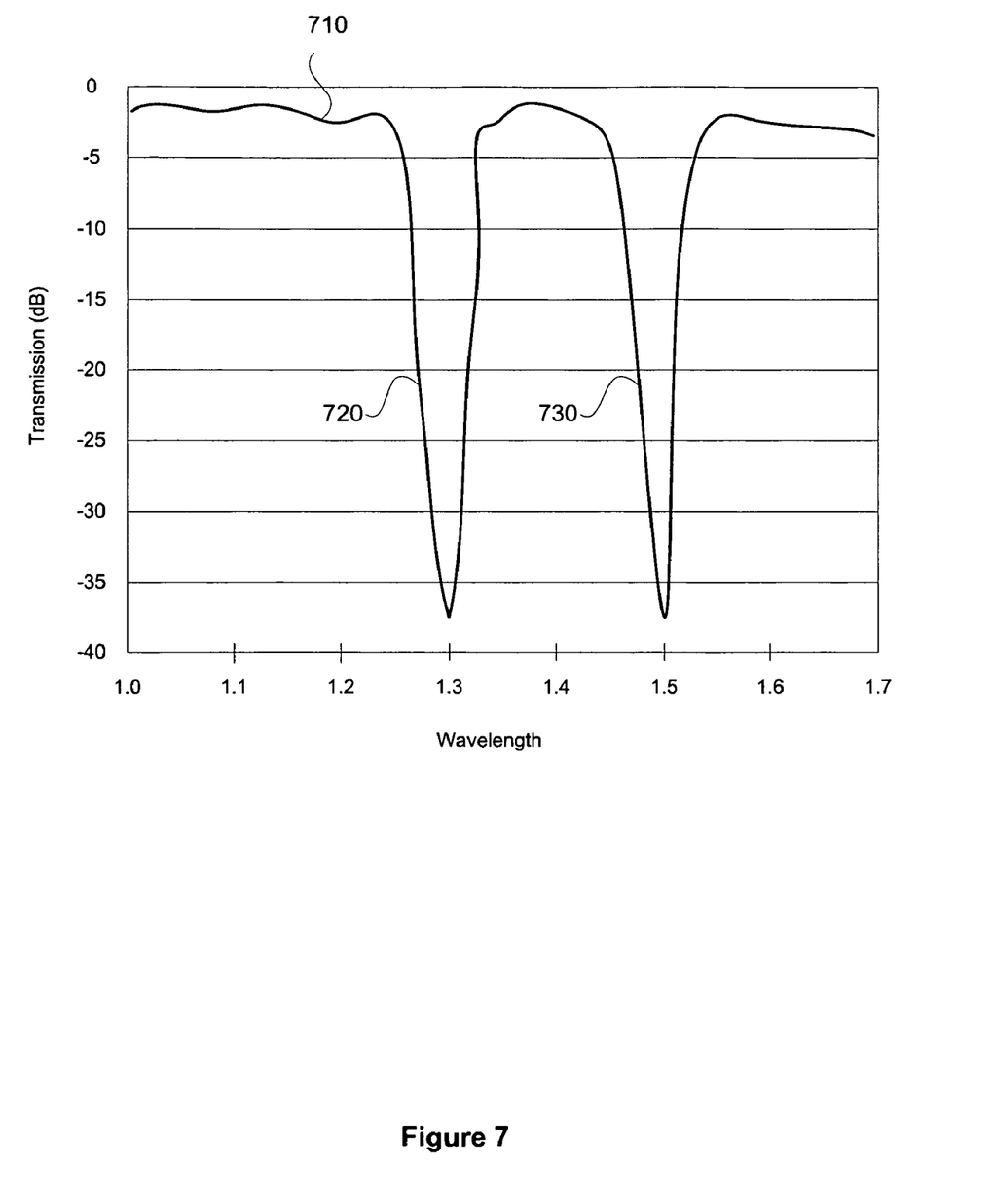
FIG. 7 is a graphical diagram illustrating a transmission response curve of the optical interferometer of FIG. 6 when configured as a multi-channel drop filter.

FIG. 7 is a graphical diagram illustrating a transmission response curve 710 of the optical interferometer 600 of FIG. 6 when configured as a multi-channel drop filter. In this embodiment, the interferometer 600 is configured to attenuate or "drop" a channel corresponding to a wavelength of 1.3 nm from the optical signal 612 input into the interferometer 600 as well as a channel corresponding to a wavelength of 1.5 nm. As shown, the dropped channels are represented by inverted spikes 720 and 730 in the transmission response curve 710. As described above in FIGS. 3 and 6, by selecting the design parameters of the interferometer 600 appropriately, the destructive interference between the diffused portions 655A and 655B and the guided portion 655B and the diffused portions 660A and 660C and the guided portion 660B necessary to attenuate or drop the pre-selected channels may be achieved. Again, in other embodiments, the interferometer 600 may be configured to drop any channels or ranges of wavelengths from the optical signal 612 by selecting design parameters such that the destructive inference necessary to drop the desired channels or ranges of wavelengths is achieved.

Although not shown, in other alternative embodiments, the interferometer 600 also may be configured to "add" channels or ranges of wavelengths to the optical signal 612 by selecting design parameters such that the constructive interference between the diffused portions 655A and 655B and the guided portion 655B and the diffused portions 660A and 660C and the guided portion 660B necessary to augment the desired channels or ranges of wavelengths is achieved. The transmission response curve 710 would show a spike (instead of the inverted spikes 720 and 730) for each added or augmented channel.

In yet an alternative embodiment, a robust filter may be created by configuring the interferometer 600 so the coupling of the guided portion 655B and the diffused portions 655A and 655C within the second MMI device 625 is substantially the same as the coupling of the guided portion 660B and the diffused portions 660A and 660C within the third MMI device 635. For example, if a transmission response similar to that of transmission response 510 were to result from the coupling of the guided portion 655B and diffused portions 655A and 655C within the second MMI device 625, and if a transmission response resulting from the coupling of the guided portion 660B and the diffused portions 660A and 660C within the third MMI device 635 were substantially the same (i.e., substantially similar to the transmission response 510), then the resulting overall transmission response of the interferometer 600 would be similar to transmission response 510. However, that transmission response would be an overall more robust and higher quality response since the same type of filtering would be performed twice, thereby providing, among other things, additional noise filtering.

Figure 8A:
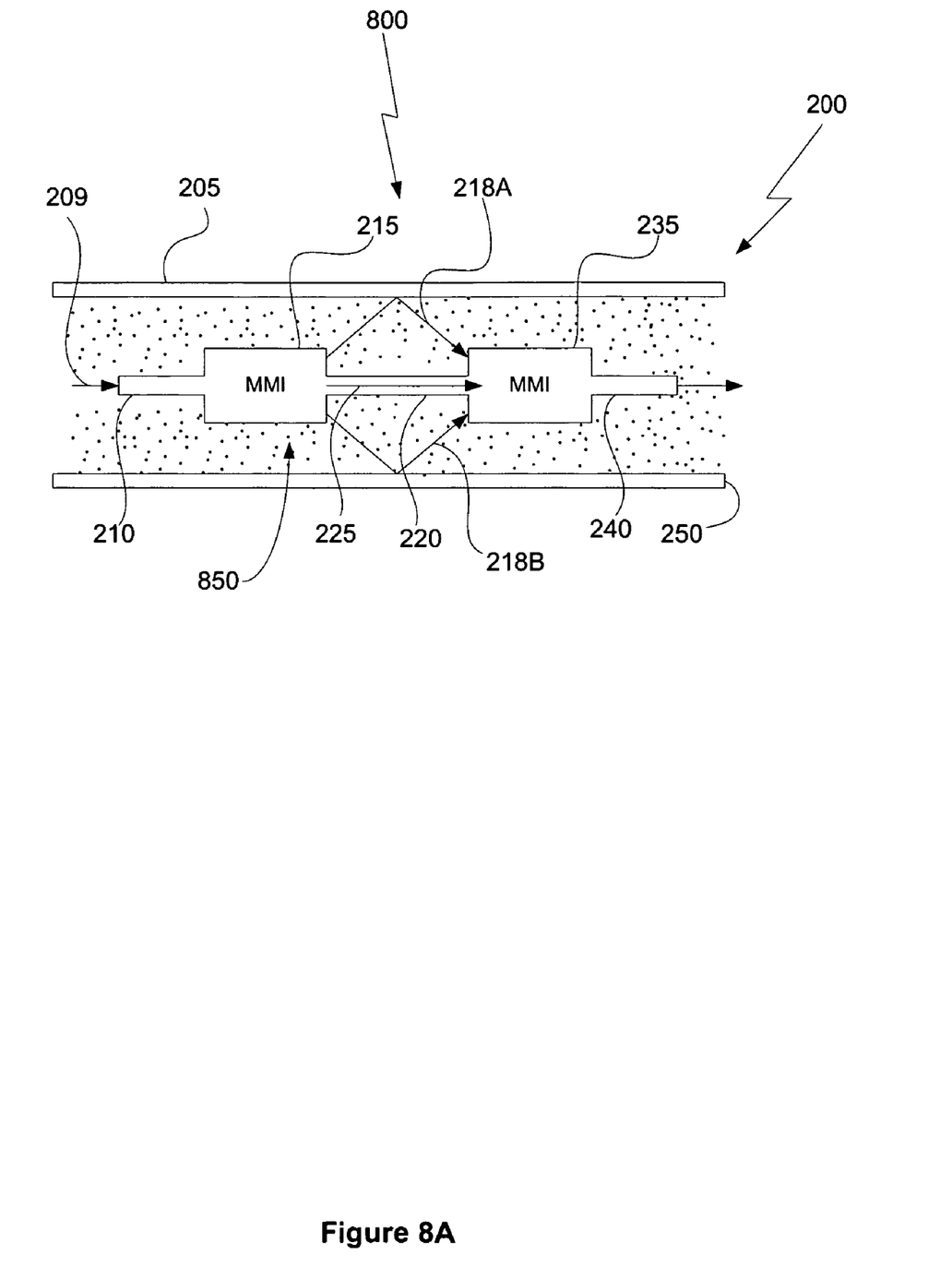
FIG. 8A is a conceptual diagram of the optical interferometer of FIG. 2 configured as a gas sensor, according to another embodiment of the invention.
Figure 8B:
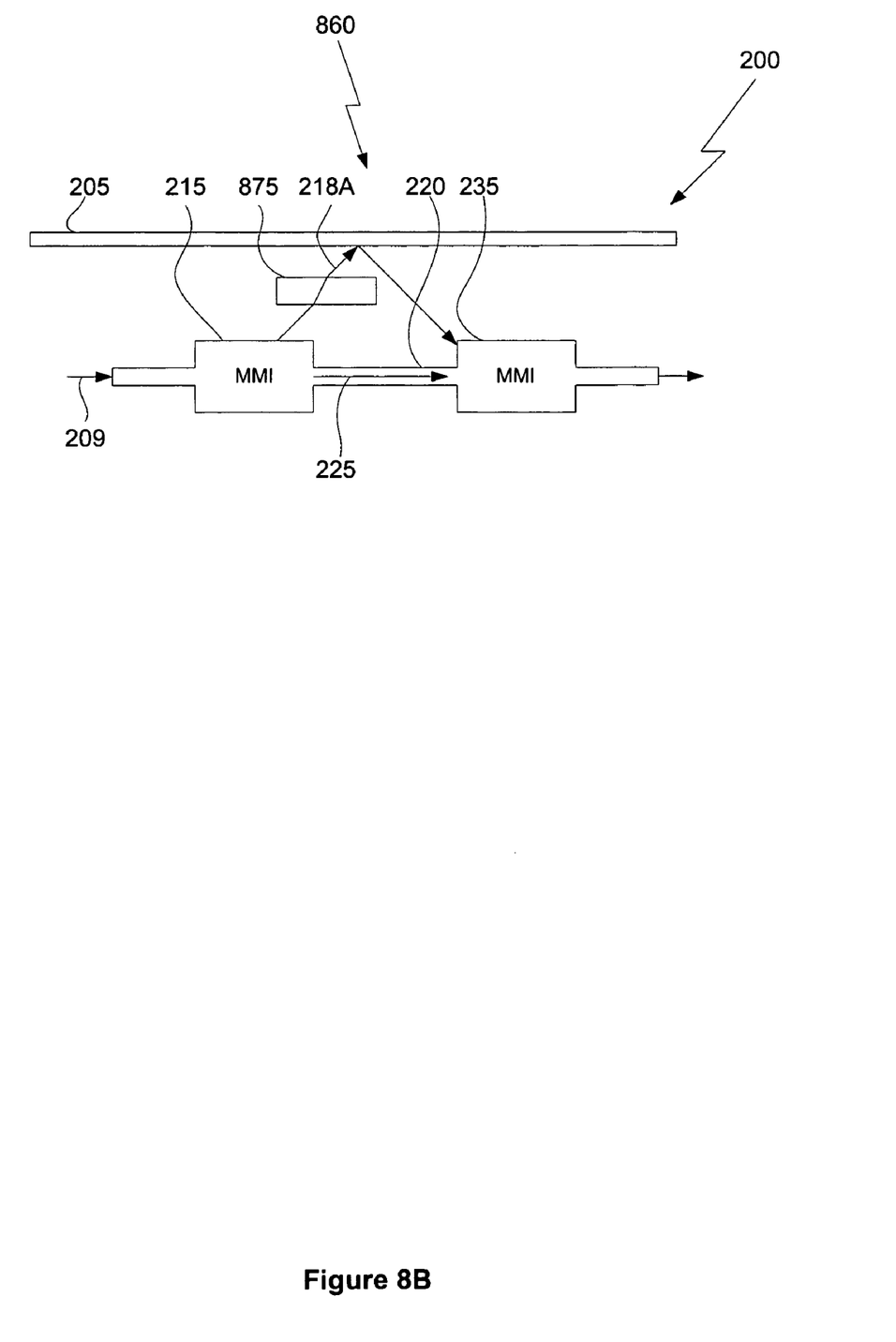
FIG. 8B is a conceptual diagram of the optical interferometer of FIG. 2 configured as a material detector, according to yet another embodiment of the invention.

As described in FIGS. 8A and 8B, the design described herein may also be used as the basis of a gas sensor or a material detector.

FIG. 8A is a conceptual diagram of the optical interferometer of FIG. 2 configured as a gas sensor 800, according to one embodiment of the invention. A gas 850 is introduced into the interferometer 200. As shown, the gas 850 is disposed between the first reflector 205 and the second reflector 250 such that the gas surrounds the first MMI device 215, the second MMI device 235 and the second waveguide 220. As previously described herein, a first signal 209 is separated by the first MMI device 215 into a guided portion 225 and diffused portions 218A and 218B. Since the gas has an associated index of refraction, the gas changes the optical path of the diffused portions 218A and 218B between the first MMI device 215 and the second MMI device 235. The change in the optical path changes the propagation time of the diffused portions 218A and 218B and, therefore, changes the phase difference between the guided portion 225 and the diffused portion 218A and 218B. The change in phase difference modifies the interference between the guided portion 225 and the diffused portions 218A and 218B within the second MMI 235 and, therefore, modifies the transmission spectrum of the interferometer 200. Thus, the interferometer 200 may be configured such that a different transmission spectrum results for each different gas introduced into the gas sensor 800. Such an approach allows an unknown gas to be identified based on the resulting transmission spectrum of the interferometer 200. For example, to determine the type of gas present in the gas sensor 800, the transmission spectrum of the interferometer 200 could be compared in a look-up table against the transmission spectra associated with several known gasses.

FIG. 8B is a conceptual diagram of the optical interferometer of FIG. 2 configured as a material detector 860, according to yet another embodiment of the invention. As shown, a cell 875 containing a sample of the material to be identified is disposed between the first waveguide 220 and the first reflector 205 of the interferometer 200. As previously described herein, the diffused portion 218A passes through the cell 875 at least once before reaching the second MMI device 235. In alternative embodiments, the cell 875 may be configured such that the diffused portion 218A passes through the cell 875 more than one time. Since the material in the cell 875 has an associated index of refraction, passing through the material changes the optical path of the diffused portion 218A between the first MMI device 215 and the second MMI device 235. The change in the optical path changes the propagation time of the diffused portion 218A and, therefore, changes the phase difference between the guided portion 225 and the diffused portion 218A. The change in phase difference modifies the interference between the guided portion 225 and the diffused portion 218A within the second MMI 235 and, therefore, modifies the transmission spectrum of the interferometer 200. Thus, the interferometer 200 may be configured such that a different transmission spectrum results for each different material introduced into the cell 875. Such an approach allows an unknown material to be identified based on the resulting transmission spectrum of the interferometer 200. For example, to determine the type of material present in the cell 875, the transmission spectrum of the interferometer 200 could be compared in a look-up table against the transmission spectra associated with several known materials.

While the foregoing is directed to embodiments of the present invention, other and further embodiments of the invention may be devised without departing from the basic scope thereof, and the scope thereof is determined by the claims that follow.

We claim:

1. An optical interferometer, comprising:
a first multimode interferometer device configured to separate a first signal into a diffused portion and a guided portion;
a second multimode interferometer device coupled to the first multimode interferometer device via a waveguide, wherein the guided portion is transmitted from the first multimode interferometer device to the second multimode interferometer device through the waveguide; and
a reflector positioned adjacent to at least half the length of the first multimode interferometer device in order to reflect at least part of the diffused portion towards the second multimode interferometer device such that the at least part of the diffused portion is coupled with the guided portion to form at least part of a second signal.

2. The optical interferometer of claim 1, wherein the at least part of the diffused portion diffuses outside of the first multimode interferometer device towards the reflector through one or more walls of the first multimode interferometer device.

3. The optical interferometer of claim 1, wherein the at least part of the diffused portion diffuses outside of the waveguide towards the reflector through a part of the wavegnide disposed proximally to the first multimode interferometer device.

4. The optical interferometer of claim 1, wherein the at least part of the diffused portion couples with the guided portion to form the at least part of the second signal within the second multimode interferometer device.

5. The optical interferometer of claim 1, wherein the at least part of the diffused portion couples with the guided portion to form the at least part of the second signal within a part of the first waveguide disposed proximally to the second multimode interferometer device.

6. The optical interferometer of claim 1, wherein a gas may be disposed between the first waveguide and the reflector, the gas causing a change in phase difference between the at least part of the diffused portion and the guided portion when coupled such that the gas may be identified based on the change in phase difference.

7. The optical interferometer of claim 1, wherein a cell of material may be disposed between the first waveguide and the reflector, the cell of material causing a change in phase difference between the at least part of the diffused portion and the guided portion when coupled such that the material may be identified based on the change in phase difference.

8. The optical interferometer of claim 1, further comprising a second reflector configured to reflect at least another part of the diffused portion towards the second multimode interferometer device such that the at least another part of the diffused portion is coupled with the guided portion to form the second signal, wherein the second reflector is disposed on a side of the waveguide that is opposite to a side on which the reflector is disposed.

9. The optical interferometer of claim 8, wherein the reflector and the second reflector are disposed equidistant from the waveguide.

10. The optical interferometer of claim 8, wherein the reflector is disposed a first distance from the waveguide and the second reflector is disposed a second distance from the waveguide, the first distance not being equal to the second distance.

11. An optical interferometer, comprising:
a first multimode interferometer device configured to separate a first signal into a diffused portion and a guided portion;
a second multimode interferometer device coupled to the first multimode interferometer device via a waveguide, wherein the guided portion is transmitted from the first multimode interferometer device to the second multimode interferometer device through the waveguide; and
a reflector configured to reflect at least part of the diffused portion towards the second multimode interferometer device such that the at least part of the diffused portion is coupled with the guided portion to form at least part of a second signal, wherein the coupling between the at least part of the diffused portion and the guided portion results in constructive interference between the at least part of the diffused portion and the guided portion.

12. The optical interferometer of claim 11, wherein the constructive interference between the at least part of the diffused portion and the guided portion causes the at least part of the second signal to have an augmented channel relative to the first signal.

13. An optical interferometer, comprising:
a first multimode interferometer device configured to separate a first signal into a diffused portion and a guided portion;
a second multimode interferometer device coupled to the first multimode interferometer device via a waveguide, wherein the guided portion is transmitted from the first multimode interferometer device to the second multimode interferometer device through the waveguide; and
a reflector configured to reflect at least part of the diffused portion towards the second multimode interferometer device such that the at least part of the diffused portion is coupled with the guided portion to form at least part of a second signal, wherein the coupling between the at least part of the diffused portion and the guided portion results in destructive interference between the at least part of the diffused portion and the guided portion.

14. The optical interferometer of claim 13, wherein the destructive interference between the at least part of the diffused portion and the guided portion causes the at least part of the second signal to have a dropped channel relative to the first signal.

15. The optical interferometer of claim 13, wherein the destructive interference between the at least part of the diffused portion and the guided portion results in a bandpass filter.

16. An optical interferometer, comprising:
a first multimode interferometer device configured to separate a first signal into a diffused portion and a guided portion;
a second multimode interferometer device coupled to the first multimode interferometer device via a waveguide, wherein the guided portion is transmitted from the first multimode interferometer device to the second multimode interferometer device through the waveguide; and
a reflector positioned adjacent to a length of the first multimode interferometer device in order to reflect at least part of the diffused portion towards the second multimode interferometer device such that the at least part of the diffused portion is coupled with the guided portion to form at least part of a second signal, wherein the reflector comprises a substantially tubular structure that encloses the waveguide 17. An optical interferometer, comprising:
a first multimode interferometer device configured to separate a first signal into a first diffused portion and a first guided portion;
a second multimode interferometer device coupled to the first multimode interferometer device via a first waveguide, wherein the first guided portion is transmitted from the first multimode interferometer device to the second multimode interferometer device through the first waveguide, and the second multimode interferometer device is configured to separate a second signal into a second diffused portion and a second guided portion;
a third multimode interferometer device coupled to the second multimode interferometer device via a second waveguide, wherein the second guided portion is transmitted from the second multimode interferometer device to the third multimode interferometer device through the second waveguide; and
a reflector configured to reflect at least part of the first diffused portion towards the second multimode interferometer device such that the at least part of the first diffused portion is coupled with the first guided portion to form at least part of the second signal and to reflect at least part of the second diffused portion towards the third multimode interferometer device such that the at least part of the second diffused portion is coupled with the second guided portion to form at least part of a third signal.

18. The optical interferometer of claim 17, wherein the coupling between the at least part of the first diffused portion and the first guided portion results in destructive interference between the at least part of the first diffused portion and the first guided portion.

19. The optical interferometer of claim 17, wherein the coupling between the at least part of the first diffused portion and the first guided portion results in constructive interference between the at least part of the first diffused portion and the first guided portion.

20. The optical interferometer of claim 17, wherein the coupling between the at least part of the second diffused portion and the second guided portion results in destructive interference between the at least part of the second diffused portion and the second guided portion.

21. The optical interferometer of claim 17, wherein the coupling between the at least part of the second diffused portion and the second guided portion results in constructive interference between the at least part of the second diffused portion and the second guided portion.

* * * * *